United States Patent [19]

Pigerol et al.

[11] 4,283,420
[45] Aug. 11, 1981

[54] PHARMACEUTICALLY ACTIVE CYCLOHEXYL COMPOUNDS AND THEIR PREPARATION

[75] Inventors: Charles Pigerol, Saint-Ouen; Jean-Claude Vernieres, Domene; Pierre Eymard, Fontaine; Jacques Simiand, Noyarey; Madeleine Broll, Saint-Egreve; Jean-Yves Lacolle, Domene, all of France

[73] Assignee: Labaz, Paris, France

[21] Appl. No.: 31,165

[22] Filed: Apr. 18, 1979

[30] Foreign Application Priority Data

Apr. 27, 1978 [GB] United Kingdom ............... 16762/78

[51] Int. Cl.³ .................. A61K 31/19; C07C 62/20; C07C 62/10; C07C 61/08
[52] U.S. Cl. .................................... 424/317; 260/464; 260/544 L; 560/126; 560/128; 562/400; 562/473; 562/491; 562/492; 562/508; 562/510; 564/123; 564/161; 564/169; 564/170; 564/171; 564/181; 564/191; 424/320; 424/324
[58] Field of Search ............... 560/102; 562/400, 507; 424/317

[56] References Cited

U.S. PATENT DOCUMENTS

| | | | |
|---|---|---|---|
| 2,404,588 | 7/1946 | Martin | 560/102 |
| 3,392,198 | 7/1968 | Paulshock | 562/400 |

FOREIGN PATENT DOCUMENTS 49-13950 12/1974 Japan ....................... 562/400

OTHER PUBLICATIONS

Tilford, J. Am. Chem. Soc., 71 p. 1705-1709 (1949).

Meerwein, Annalen, 419 p. 159-175.
Reichstein, Helv. Chem., 18 p. 721-724 (1935).
Shive, J. Am. Chem. Soc. 63 p. 2979-2984 (1941).
Tarbouriech, Compt. Rewd. 150 p. 1606-1607.

*Primary Examiner*—Natalie Trousof
*Assistant Examiner*—Michael Shippen
*Attorney, Agent, or Firm*—Mason, Kolehmainen, Rathburn & Wyss

[57] ABSTRACT

The chemical compounds of the invention are useful as the active compound in drugs because of their anticonvulsant and/or antianoxic activity. They have the general formula

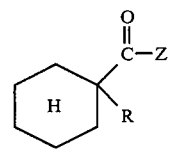

wherein Z is a hydroxyl group; a group—OM wherein M is an alkali metal atom or an equivalent atom fraction of an alkaline-earth metal or an amino group such as —NH₂, and R is a linear or branched alkyl group containing from 1 to 9 carbon atoms, and optionally substituted by one or more halogen atoms; a linear or branched alkenyl or alkynyl, alkoxyalkyl, or acylalkyl group containing from 2 to 9 carbon atoms and optionally substituted by one or more halogen atoms; an aryl or arylalkyl or aryloxyalkyl group comprising at least one aromatic radical and an alkyl chain having from 1 to 4 carbon atoms.

3 Claims, No Drawings

PHARMACEUTICALLY ACTIVE CYCLOHEXYL COMPOUNDS AND THEIR PREPARATION

FIELD OF THE INVENTION

The present invention is concerned with certain cyclohexylcarboxylic acids and derivatives thereof and with their preparation and with their pharmacological use.

SUMMARY OF THE INVENTION

The chemical compounds according to the invention have the general formula:

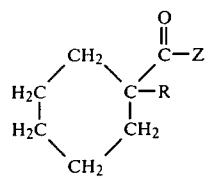
(1)

which in the remainder of the description will be simplified to

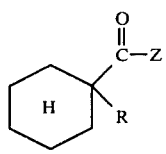
(1)

in which:

Z is a hydroxyl group, in which case the compound (1) is an acid; a group OM, in which M is an alkali metal atom, such as Na, K or Li, or an equivalent atom fraction of an alkaline earth metal atom, such as Mg or Ca, in which case the compound (1) is a metal salt; or an amino group —$NH_2$, in which case the compound (1) is an amide, and R is a linear or branched alkenyl, alkynyl, alkoxyalkyl, or acylalkyl group, containing from 2 to 9 carbon atoms and optionally substituted by one or several halogen atoms, or an aryl, an/arylalkyl or aryloxyalkyl group comprising at least one substituted or unsubstituted aromatic group such as the phenyl group and an alkyl chain comprising from 1 to 4 carbon atoms.

It has been discovered that these compounds are useful especially in the pharmaceutical field as active compounds in the treatment of diseases of the central nervous system because of their pharmacological properties and more specially their anticonvulsivant and/or antianoxic activities and their low toxicity. A similar activity has been also found for compounds having the same general formula wherein however R may also be a linear or branched alkyl group comprising from 1 to 4 carbon atoms and optionally substituted by one or several halogen atoms.

Therefore new pharmaceuticals according to the invention comprise as the active agent in a pharmaceutically acceptable carrier at least one compound having the general formula

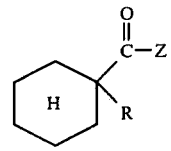

wherein Z has the above stated meaning and R is a linear or branched alkyl group containing from 1 to 9 carbon atoms, and optionally substituted by one or more halogen atoms; a linear or branched alkenyl or alkynyl, alkoxyalkyl, or acylalkyl group containing from 2 to 9 carbon atoms and optionally substituted by one or more halogen atoms; an aryl or arylalkyl or aryloxyalkyl group comprising at least one aromatic radical and an alkyl chain having from 1 to 4 carbon atoms.

In the above formula, the halogen substituent may be preferably fluorine, bromine or chlorine, the metal in the OM group may be preferably Na, K, Mg or Ca, and R may be preferably one of the following groups:

a linear alkyl group such as the methylethylpropyl groups;

a branched alkyl group such as the isopropyl, isobutyl, t-butyl groups;

an alkenyl group of the formula

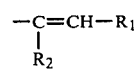
(2)

(3)

in which $R_1$ is a hydrogen atom or linear or branched alkyl group containing up to 6 carbon atoms and $R_2$ is a hydrogen atom or a linear alkyl group comprising from 1 to 3 carbon atoms; an alkynyl group of the formula:

(4)

or

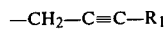
(5)

in which $R_1$ has the above-stated meanings; a linear or branched haloalkyl group of the formula

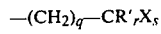
(6)

in which X is a halogen atom, such as chlorine or bromine, R' is a hydrogen atom or an alkyl group containing 1 to 3 carbon atoms, q and r, which may be the same or different, are 0, 1 or 2, and s is 1, 2 or 3, the sum of r and s being 3; a haloalkenyl group of the formula

(7)

in which t may be 0 or 1, Y' and Y'' are either a hydrogen atom or a halogen atom, while one of them at least is a halogen atom such as chlorine or bromine, and R' has the above-stated meaning; an alkynyl group of the formula

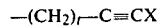
(8)

in which t and X have the above-stated meanings;

an alkoxymethyl group of the formula $$-CH_2-O-R_3 \quad (9)$$

wherein $R_3$ is an alkyl group containing up to 7 carbon atoms which may be linear or branched such as the methyl group or the isopropyl group;
an acylmethyl group of the formula $$-CH_2-CO-R_4 \quad (10)$$

in which $R_4$ is a linear or branched alkyl group having 1 to 4 carbon atoms;
a 2-halo-acylmethyl group of the formula $$-CH_2-CO-CHX-R_5 \quad (11)$$

in which X has the above-stated meaning, and $R_5$ is a hydrogen atom or a linear or branched alkyl group having 1 to 3 carbon atoms;
an aralkyl group of the formula $$-(CH_2)_q-Ar \quad (12)$$

in which q is 0, 1 or 2 as already stated above and Ar is a substituted or unsubstituted aromatic group, such as a phenyl group;
an aryloxyalkyl group of the formula $$-(CH_2)_{q'}-O-Ar \quad (13)$$

wherein Ar has the above-stated meaning and $q'$ is 1 or 2.

The pharmaceutically active compounds of the invention may be used in any known drug form in admixture with usual carriers. They may be used for instance in the form of pills, tablets, capsules, solutes, sirups, suppositories, solutions. They may be administered by any known means, for instance, orally or by IM, SC or IV injection. In their uses as anticonvulsant or antianoxic agents, or more generally in the treatment of diseases involving the central nervous system such as epilepsy and other neuro-psychic disturbances, they may be administered to humans at daily doses varying typically from 200 to 3000 mg, and most often around a mean value of about 1000 mg.

The compounds according to the invention may be prepared from the cyclohexylcarboxylic acid or from the derivatives of this acid.

A method according to the invention for preparing the compounds of formula (1), useful as active agents for drugs, comprises reacting cyclohexylcarboxylic acid or a nitrile or ester thereof with a strong base to form an organometallic derivative, reacting said organometallic derivative with a compound having formula R—Y wherein Y is a halogen atom such as chlorine or bromine, or with a compound containing a functional group adapted to react with the organometallic derivative, such as an acid anhydride halide, an aldehyde or a ketone, thereby obtaining a cyclohexylcarboxylic acid, nitrile or ester, carrying an R substituent in the α position, optionally modifying this substituent on the cyclohexyl ring by reactions known per se, and optionally converting the compound obtained from an ester into the corresponding cyclohexylcarboxylic acid and/or from an acid into a pharmaceutically acceptable salt or amide.

The substituent R on the compounds obtained by the reaction on the organometallic derivative may have any of the meanings already indicated for the pharmaceutically active agents having formula (1), but it may also be an acyl group or a hydroxyalkyl group comprising from 1 to 9 carbon atoms, in new chemical compounds which are useful as intermediates in the preparation of such pharmaceutically active agents, and which are also within the scope of the present invention.

DETAILED DESCRIPTION OF THE INVENTION

The preferred embodiments of the method of the invention vary according to the structure of the group R with a bound from the beginning in its final form on the cyclohexane ring whether modified afterwards. It should be pointed out in particular that ketone groups may preferably be formed from the corresponding acetylenic groups once bound on the cyclohexane ring and that ethylenic groups may preferably be formed from corresponding halo or hydroxy groups, and more specifically from halo groups as defined in connection with the formula (1) of active compounds, or from alkyl groups further comprising an OH substituent in the α position of the cyclohexane ring.

A number of specific embodiments of the method of the invention will be described hereinafter, first for the compounds of the invention which are acids, then for the preparation of the compounds which are salts from such acids, and for the preparation of the compounds which are amides from such acids or from nitriles thereof.

Acids of formula (1) in which R is an alkyl group, an alkenyl group, of formula (3), an alkynyl group, an alkoxyalkyl group, an haloalkyl group, an haloalkenyl group, an aralkyl group or an aryloxyalkyl group, can be prepared using cyclohexylcarbonitrile of the formula

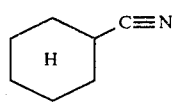

or cyclohexylcarboxylic acid of the formula

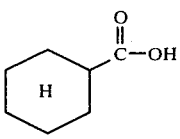

or esters of this acid, such as methyl or ethyl esters, as the starting material. The intermediate compounds having formula (1) wherein R is an acyl group or a hydroxyalkyl group can be prepared in the same way. The acids thus prepared will be referred to hereinafter as "acids of type A".

The acids of formula (1) in which R is an alkoxyalkyl group, an acylalkyl group, a haloacylalkyl group, an alkenyl group of formula (2), which will be hereinafter referred to as "acids of type B" can be prepared from acids of type A or from derivatives of such acids, especially nitriles or esters.

1. Preparation of acids of type A

1.1. Using cyclohexylcarbonitrile as the starting material

A preferred process involves three stages, as follows: Cyclohexylcarbonitrile (17) is reacted with a strong base, for example sodium amide or a lithium dialkylamide, so as to form a cyclohexylcarbonitrile metallised with sodium or lithium in the α position (19). The latter compound (19) is then reacted with a compound of the formula R—Y (20), in which R has the same meaning as in formula (1) and Y is a halogen atom, so as to form a substituted cyclohexylcarbonitrile (21). The latter compound is then hydrolysed to an α-substituted cyclohexylcarboxylic acid of formula (1) by the action of a dilute mineral acid (for example 50% aqueous sulphuric acid).

This process can be represented schematically as follows:

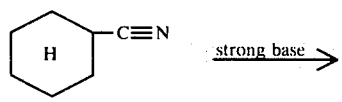

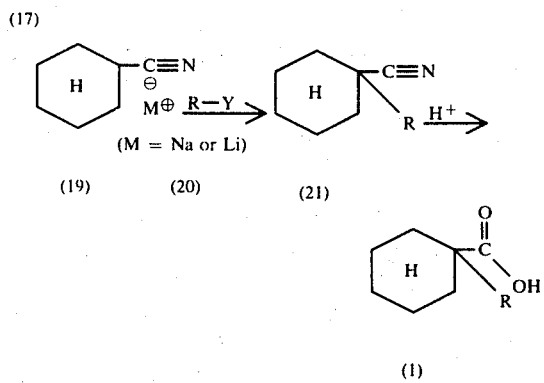

To obtain a compound of formula (19) in which M is sodium, sodium amide in liquid ammonia is preferably used to metallise the cyclohexylcarbonitrile. A suitable solvent for use in this stage and in the following stage (reaction between derivatives (19) and (20)) is, for example, 1,2-dimethoxyethane.

To obtain a compound of formula (19) in which M is lithium, metallisation is preferably effected using a lithium dialkylamide (such as lithium diethylamide or lithium di-isopropylamide), which may be prepared in a mixture of hexamethylphosphoric acid triamide (HMPT) and benzene and under nitrogen, using lithium and the desired dialkylamine as the starting material.

In general, the reaction of the base with the cyclohexylcarbonitrile (17) may be carried out at about −40° C. and the reaction between the compounds of formulae (19) and (20) may be carried out at about −20° C.

1.2. Using cyclohexylcarboxylic acid (or ester thereof) as the starting material A preferred process involves two stages, as follows (plus a hydrolysis step when starting from an ester):

Cyclohexylcarboxylic acid is reacted with a strong base (such as a lithium dialkylamide, preferably lithium diisopropylamide), so as to form a cyclohexylcarboxylic acid which is metallised with lithium in the α-position of formula (22). The latter compound is then reacted, in an acid medium, with a compound of the formula R—Y (20), as defined above, so as to obtain an α-substituted cyclohexylcarboxylic acid of formula (1).

This process can be represented schematically as follows:

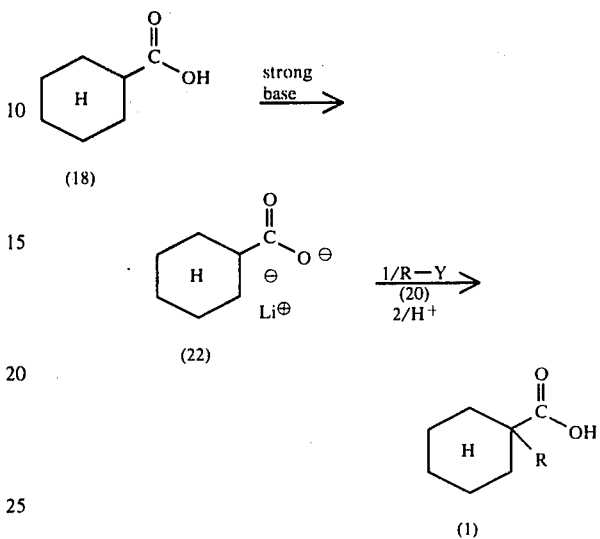

Lithium dialkylamides prepared in a mixture of solvents, such as tetrahydrofuran/hexane, at −10° C. under a nitrogen atmosphere, from butyl-lithium and the desired dialkylamine may be used as the strong base. The reaction of this base with cyclohexylcarboxylic acid (18) may, for example, be carried out in tetrahydrofuran at a temperature of from −10° to +50° C. The reaction between the compounds (20) and (22) may, for example, be carried out at −70° C.

2. Preparation of acids of type B

Generally speaking, the methods of preparation which will now be described, essentially comprise the modification of a group R previously fixed in the α position on the cyclohexylcarboxylic acid or on the nitrile thereof, or on one of the esters thereof, especially the ethylic or methylic esters. They may also often be used as alternative methods for the preparation of the acids of type A. The group R in the starting compound may have the same meanings as those already indicated for the formula (1) of the active compounds. It may thus be especially an alkyl group, an alkenyl group, a haloalkyl group, a haloalkenyl group, an alkynyl group, or an acylalkyl group. But it may also have other meanings in new compounds which are used as intermediates in the preparation of the active compounds and which have the same formula (1) wherein however a group R may be a hydroxyalkyl group or an acyl group of the type —C(R$_2$)OH—R″ or —CO—R″ wherein R″ is a linear or branched alkyl group comprising from 1 to 8 carbon atoms and R$_2$ is a hydrogen atom or a linear alkyl group comprising from 1 to 3 carbon atoms. The fixation of the group R in the starting compounds for the preparation of acids of type B may occur through the formation of an intermediate organometallic derivative and the reaction of the latter with a compound R—Y wherein Y is a halogen atom, an acid anhydride halide YCOR″, a ketone or an aldehyde having formula R″COR$_2$, according to any of the specific procedures already described in connection with the preparation of acids of type A.

The various methods of preparation of acids of type B will now be described, depending on the nature of the R radical.

2.1. R is an alkenyl group of formula (2)

The method involves as an intermediate an ester of the cyclohexylcarboxylic acid carrying in the α position a radical of formula —CHOH—$R_1$ wherein $R_1$ has the same meaning as stated above for formula (2), according to the following reactions, starting from the methyl or ethyl cyclohexane carboxylate.

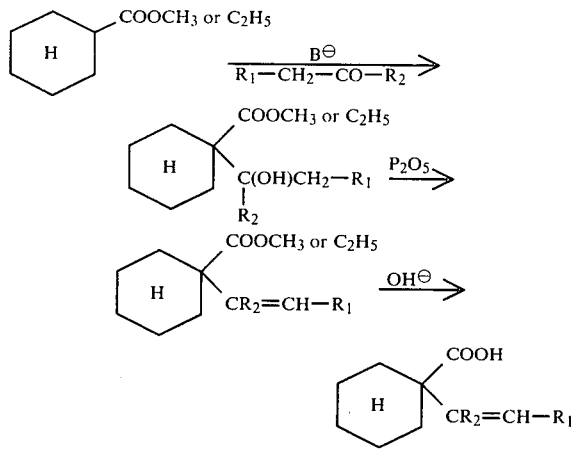

This method thus comprises the following 4 steps:
reaction of an aldehyde or a ketone on the methyl or ethyl cyclohexanecarboxylate in the presence of a base so as to obtain the hydroxyester according to a reaction similar to that of the preparation of acids of type A;
dehydration of the hydroxyester into the ethylenic ester by the action of phosphoric anhydride;
saponification of the ethylenic ester into the ethylenic acid.

2.2. R is a haloalkyl group 2.2.1 The compounds of the invention wherein R is a haloalkyl group with a halogen atom in the α position of the cyclohexyl ring may be obtained by reaction a hydrogen halide on a corresponding acid alcohol compound which is in turn obtained by the same route as the acids of type A by reacting an aldehyde or a ketone with the cyclohexylcarboxylic acid or the esters thereof. The procedure described in French Patent No. 1 231 163 filed on Apr. 8, 1959 by Kodak Pathe may for instance be used.
The reaction of a ketone on the cyclohexylcarboxylic acid in the presence of a strong base leads to a hydroxy substituted branched alkyl group which is then converted into the corresponding halo group according to the reactions:

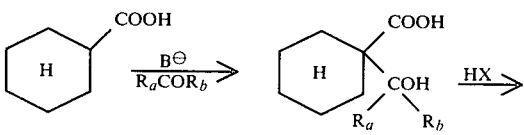

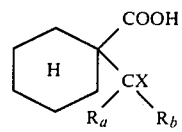

wherein $R_a$ and $R_b$ are linear or branched alkyl groups comprising from 1 to 6 carbon atoms.

2.2.2 In the specific case when radical R is of the type —$CH_2X$, it is also possible to start from di(hydroxymethyl)cyclohexane by reacting same with a hydrogen halide HX while one of the alcohol functional groups is temporarily protected as its acetyl derivative, and then oxidizing the remaining alcohol function into the acid.

2.3. R is a haloalkenyl group

Beside the method of preparation of the acids of type A which may be used for instance when R has the formula (7) wherein t is 1, Y' is a halogen atom, X and Y" is a hydrogen atom, it is also possible, for instance when in formula (7) t is 0, Y' is a halogen atom X and Y" is a hydrogen atom, to react phosphorus pentachloride in an anhydrous medium with an intermediate compound wheren R is an acyl group of the type —CO—$CH_2R'$, the latter being obtained by reacting the corresponding acid anhydride chloride with an ester of a cyclohexylcarboxylic acid.

2.4. R is an alkynyl group

Beside the process described for the acids of type A, the acids of type B wherein R is an alkynyl group may be obtained for instance by dehydrohalogenating haloalkenyl groups of formula (7) carried by an ester of cyclohexylcarboxylic acid or by the acid proper, according to the reactions:

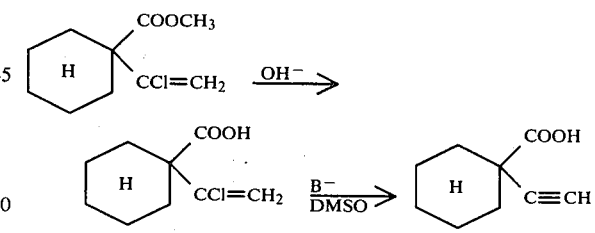

2.5. R is a haloalkynyl group

The cyclohexylcarboxylic acids of formula (1) having in the α position a haloalkynyl subtituent can be prepared from the convenient 1-alkynyl-1-cyclohexyl carboxylic acids when the triple bound is at the end of the chain, i.e. from the compounds of formula (1) in which R is an alkynyl group of formula (4) or (5) wherein $R_1$ is H, by reacting the sodium derivative thereof with an alkaline metal hypohalide of the formula XOM in which X and M have the meanings indicated above, or with benzene sulfonyle chloride (in this latter case, X must be Cl). The compounds of formula (1) having a R group of formula (8) can be prepared by this method as follows:

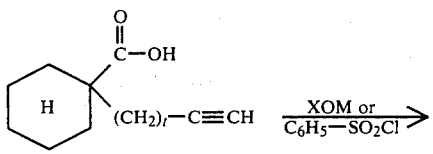

(1)     t = 0 or 1

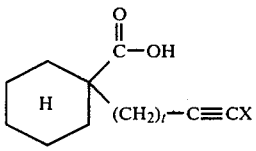

(1)

2.6. R is a dihaloalkenyl group

When for instance the group R according to formula is —$CH_2$—CBr=CHBr the compound can be prepared by reacting the acid of formula (1) wherein R is —$CH_2$—C≡CH with bromine in carbontetrachloride.

2.7. R is an acylalkyle group

These commmpounds can be obtained from the acids of formula (1) wherein R is an acetylenic group or the esters thereof. For instance, in order to obtain the group R of formula (10), the reaction sequence may be as follows, with $R_4$ being —$CH_2R_1$ and $R_1$ being such as stated above for formula (5):

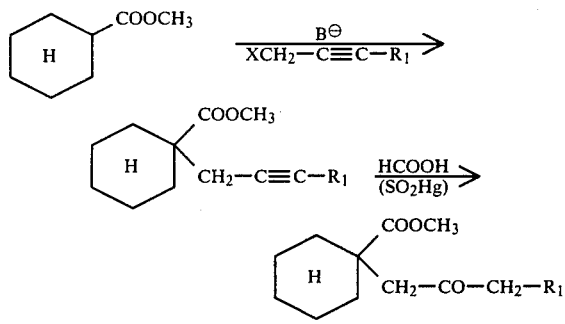

The ester is then hydrolised.

A similar conversion of group R from an acetylenic group into a keto group can also be carried out on the acetylenic acid proper.

2.8. R is a haloacylalkyl group

These compounds may be prepared by reaction of bromine on the corresponding acylalkyl group according to the reaction:

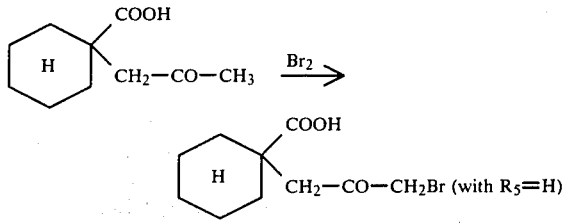

2.9. R is a tertiary alkyl group

These compounds can be prepared by reacting a compound RX, wherein R is the tertiary alkyl group and X is a halogen atom, with an intermediate compound formed by reacting trimethylsilylchloride with an ester of cyclohexylcarboxylic acid and then hydrolising the ester obtained.

3. Preparation of the alkali metal and alkaline earth metal salts

Typical methods of preparation of these salts are described below.

3.1. The addition of the acid to an aqueous solution of the base, the salt formed being isolated by atomisation of the aqueous solution containing it.

3.2. Reaction of a methanolic solution of the base with a solution of the acid in toluene. After neutralising, the water formed is eliminated by distilling off the water/toluene azeotrope. The salt becomes insoluble in the toluene and is subsequently separated by drying.

3.3. Reaction of a metal alcoholate with the acid in an alcoholic medium, the salt being isolated by concentration or drying.

4. Preparation of the amides

Typical methods of preparation of these compounds are described below:

4.1. An acid of formula (1) is converted to the corresponding anhydride chloride by means of a chlorinating agent (for example, thionyl chloride, phosphorus oxychloride, phosphorus trichloride or phosphorus pentachloride) in accordance with the equation:

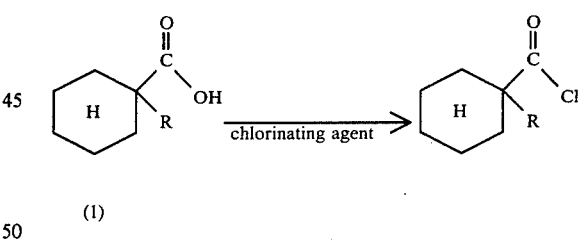

(1)

followed by conversion of the anhydride chloride to the corresponding amide by reaction with ammonia, in accordance with the equation:

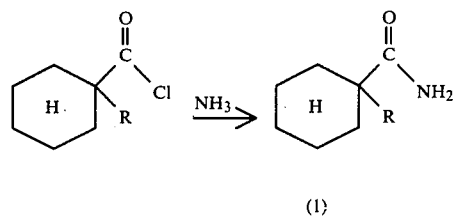

(1)

4.2. A nitrile of formula (21) is subjected to acid hydrolysis, using an acid such as sulphuric acid, in accordance with the equation:

$$\underset{(21)}{\text{[cyclohexyl with H, R, C≡N]}} \xrightarrow[H_2SO_4]{80\%} \underset{(1)}{\text{[cyclohexyl with H, R, C(=O)NH}_2\text{]}}$$

In order that the invention may be more fully understood, the following Examples are given by way of illustration only. The abbreviations used in the Examples have the following meanings: b.p.: boiling point, m.p.: melting point and n: refractive index.

EXAMPLE 1

1-Allyl-1-cyclohexyl-carboxylic acid 300 cm$^3$ of dry tetrahydrofuran (THF) and 40 g of diisopropylamine redistilled over calcium hydride were introduced into a 1 liter three-necked flask fitted with a condenser closed with a calcium chloride guard tube, a low-temperature thermometer, a mechanical stirrer and a nitrogen inlet tube. The solution was cooled to $-20°$ C. and 220 cm$^3$ of a 1.47 M solution of butyl-lithium in hexane were added. The addition was made in the course of 1 hour; the temperature of the mixture was kept at $-10°$ C. 25.5 g (0.2 mole) of 1-cyclohexyl-carboxylic acid, dissolved in 50 cm$^3$ of dry THF, were then introduced in the course of 20 minutes and the temperature of the whole was then raised gradually to 50° C. and this temperature was maintained for 2 hours. The yellow solution was cooled to $-70°$ C. 15.3 g of dry allyl chloride were added and the mixture was stirred for a further 2 hours whilst allowing the temperature to return to ambient temperature, after which the whole was left to stand for 12 hours. The solution was concentrated in vacuo and then poured into 100 cm$^3$ of ice-cold distilled water and 100 cm$^3$ of hexane. The aqueous phase, which had been separated off, was acidified with dilute hydrochloric acid. The 1-allyl-1-cyclohexylcarboxylic acid obtained was extracted with ether. It was purified by distillation under reduced pressure and was in the form of a colourless liquid.

b.p.$_{1\ mm\ Hg}$: 108°–110° C.
Weight: 18 g.
Yield: 57%.

EXAMPLE 2

1-(2′-Chloro-2′-propenyl)-cyclohexylcarboxylic acid

This compound was prepared by a method analogous to that described in Example 1.

b.p.$_{0.8\ mm\ Hg}$: 130° C.
Yield: 60%.

EXAMPLE 3

1-Propargyl-1-cyclohexyl-carboxylic acid 300 cm$^3$ of dry tetrahydrofuran (THF) and 267 cm$^3$ of 1.47 M solution of butyl-lithium in hexane were introduced into a 1 liter three-necked flask, which was kept under a nitrogen atmosphere. 40 g of anhydrous diisopropylamine and then 25.6 g (0.2 mole) of cyclohexylcarboxylic acid, dissolved in 50 cm$^3$ of THF, were added to the mixture, which had been cooled to $-20°$ C. The mixture was heated at 60° C. for 2 hours. 23.6 g of propargyl bromide were then added to the solution which had been cooled to $-70°$ C. When the mixture had warmed to ambient temperature, it was concentrated under reduced pressure and the resulting product was taken up in water. The aqueous solution was washed with hexane and then treated with dilute hydrochloric acid. The expected 1-propargyl-1-cyclohexylcarboxylic acid, which was in the form of a colourless liquid, was extracted with ether and then distilled in vacuo.

b.p.$_{0.05\ mm\ Hg}$: 110°–112° C.
Yield: 37%.

EXAMPLE 4

1-Methoxymethyl-1-cyclohexyl-carboxylic acid 11.8 g (0.093 mole) of cyclohexylcarboxylic acid were added to a solution of lithium diisopropylamide prepared using 125 cm$^3$ of a 1.50 M solution of butyllithium in hexane, 18.9 g of diisopropylamine and 200 cm$^3$ of THF as the starting materials. After the mixture had been heated at 60° C. for 2 hours, 8 g of methoxymethyl chloride were added, at a temperature of $-30°$ C. After the customary treatment, methoxymethylcyclohexylcarboxylic acid was distilled; this was in the form of a colourless liquid which crystallised on cooling.

b.p.$_{0.5\ mm\ Hg}$: 105°–106° C.
Yield: 40%.
m.p.: 35° C.

EXAMPLE 5

1-Isopropoxymethyl-1-cyclohexyl-carboxylic acid 1-isopropoxymethyl-1-cyclohexyl-carboxylic acid was prepared by a method analogous to that of Example 4.

b.p.$_{0.02\ mm\ Hg}$: 110°–112° C.

EXAMPLE 6

1-Benzyl-1-cyclohexyl-carboxylic acid

A solution of lithium diisopropylamide was prepared in the conventional manner using 266 cm$^3$ of a 1.50 M solution of butyl-lithium in hexane and 56 g of isopropylcyclohexylamine in 300 cm$^3$ of THF as the starting materials. 25.2 g (0.2 mole) of cyclohexylcarboxylic acid were added and the whole was heated at 50° C. for 2 hours, after which 23.3 g of benzyl chloride were introduced slowly, at $-20°$ C.

The 1-benzyl-cyclohexylcarboxylic acid obtained was purified by redistillation and was in the form of a colourless liquid which crystallised, on cooling, as colourless crystals.

b.p.$_{0.05-0.06\ mm\ Hg}$: 132°–135° C.
Yield: 60%.
m.p.: 77°–78° C.

EXAMPLE 7

1-Ethyl-1-cyclohexyl-carboxylic acid (1) 1-Ethyl-1-cyclohexyl-carbonitrile

A suspension of sodium amide in liquid ammonia (Organic Reactions Coll. Volume III, page 291) was prepared in a 2 liter three-necked flask using 27.6 g of sodium and 1 liter of ammonia as the starting materials. 109 g (1 mole) of cyclohexanecarbonitrile, dissolved in 100 cm$^3$ of dry dimethoxyethane (DME), and then 130 g of ethyl bromide, dissolved in 100 cm$^3$ of DME, were added to the suspension of amide. The halide was added in the course of 15 minutes and gave rise to a vigorous evolution of gaseous ammonia. The ammonia was then evaporated by heating by means of a bath of tepid water. The residual mixture was treated with 300 cm$^3$ of ether and 200 cm$^3$ of water. The aqueous phase, which had been separated off, was extracted with twice 100 cm$^3$ of ether. The ethereal phases were concentrated and the residual oil, which was dissolved in 500 cm$^3$ of hexane, was washed twice with 100 cm$^3$ of 10% hydrochloric acid and then twice with 100 cm$^3$ of a saturated solution of sodium chloride. After drying over magnesium sulphate, the organic solution was concentrated. The desired 1-ethyl-1-cyclohexyl-carbonitrile was distilled and was in the form of a colourless liquid.

b.p.$_{13\ mm\ Hg}$: 81° C.
Yield: 83%.

(2) 1-Ethyl-1-cyclohexyl-carboxylic acid

A mixture of 12 g (0.0876 mole) of the 1-ethyl-1-cyclohexyl-carbonitrile resulting from the preceding stage and 200 cm$^3$ of 50% sulphuric acid was heated at a temperature of 140° C. for 20 hours, whilst stirring vigorously. The organic phase was extracted, in the cold, with benzene. After evaporating off the solvent, the mixture was taken up in 150 cm$^3$ of water and 20 cm$^3$ of concentrated sodium hydroxide solution. The basic aqueous solution was washed with ether and then acidified. After extracting with benzene and drying over magnesium sulphate, the solvent was evaporated off. The oil obtained was distilled under reduced pressure. The 1-ethyl-1-cyclohexyl-carboxylic acid was a colourless oil.

b.p.$_{0.5\ mm\ Hg}$: 100° C.
Yield: 80%.
m.p.: 39° C.

EXAMPLE 8

1-Propyl-1-cyclohexyl-carboxylic acid

1-Propyl-1-cyclohexyl-carbonitrile (b.p.$_{13\ mm\ Hg}$: 94° C.) and then 1-propyl-1-cyclohexyl-carboxylic acid (m.p.: 58°–59° C.) were prepared successively by a method analogous to that of Example 7.

EXAMPLE 9

1-Isopropyl-1-cyclohexyl-carboxylic acid

1-Isopropyl-1-cyclohexyl-carbonitrile (b.p.$_{15\ mm\ Hg}$: 100° C.) and then 1-isopropyl-1-cyclohexylcarboxylic acid (m.p.: 102° C.) were prepared successively by a method analogous to that of Example 7.

EXAMPLE 10

1-Isobutyl-1-cyclohexyl-carboxylic acid

1-Isobutyl-1-cyclohexyl-carbonitrile (b.p.$_{15\ mm\ Hg}$: 112° C.) and then 1-isobutyl-1-cyclohexylcarboxylic acid (b.p.$_{0.1\ mm\ Hg}$: 102°–104° C.) were prepared successively by a method analogous to that of Example 7.

EXAMPLE 11

1-Ethynyl-1-cyclohexyl-carboxylic acid

A suspension of sodium amide in liquid ammonia was prepared using 3.5 g of sodium. After evaporating off the ammonia, the sodium amide was dissolved in 40 cm$^3$ of anhydrous dimethylsulphoxide (DMSO). The mixture was stirred under nitrogen for 3 hours and a solution of 6.6 g (0.035 mole) of 1-(1-chlorovinyl)-1-cyclohexyl-carboxylic acid in 30 cm$^3$ of dry DMSO was added slowly. The temperature of the whole was raised to 50° C. in the course of 6 hours and stirring was continued overnight at laboratory temperature. The mixture was poured into a cold solution of 20% hydrochloric acid. The resulting mixture was extracted several times with ether. After evaporating off the solvent, 1-ethynyl-1-cyclohexyl-carboxylic acid was obtained and this crystallized as colourless crystals on the addition of pentane.

m.p.: 63° C.
Yield: 66%.

EXAMPLE 12

1-(1'-Chlorovinyl)-1-cyclohexyl-carboxylic acid (1) Methyl 1-acetyl-1-cyclohexyl-carboxylate This compound was prepared in accordance with the method for the preparation of keto-esters described by: M. W. Rathke and J. Deith in *Tetrahedron Letters*, 1971, 31, page 2,953.

500 cm$^3$ of a 1.50 M solution of butyl-lithium in hexane were introduced into a 2 liter three-necked flask. 106 g of anhydrous N-cyclohexylisopropylamine (redistilled over calcium hydride) and 300 cm$^3$ of dry tetrahydrofuran (THF) were added, under a nitrogen atmosphere, to the mixture, which had been cooled to −10° C. The mixture was stirred for 20 minutes and 106.5 g (0.75 mole) of methyl cyclohexyl-carboxylate were then added, at −40° C. The temperature of the mixture was lowered to −70° C. and 59 g of acetyl chloride were introduced slowly. When the mixture has warmed to ambient temperature, it was acidified and the THF was evaporated off under a partial vacuum. The residue was taken up in water; the resulting methyl 1-acetyl-1-cyclohexyl-carboxylate was extracted with ether and purified by double distillation, giving a colourless liquid.

b.p.$_{5\ mm\ Hg}$: 100°–101° C.
Yield: 27%.

(2) Methyl 1-(1'-chlorovinyl)-1-cyclohexylcarboxylate 23.5 g of methyl 1-acetyl-1-cyclohexyl-carboxylate dissolved in 100 cm$^3$ of dry methylene chloride were heated under reflux for 6 hours in the presence of 30 g of phosphorus pentachloride. The mixture was then poured on to ice. The methylene chloride solution was separated off and washed with water and then with bicarbonate. After drying over magnesium sulphate, the solution was concentrated and methyl 1-(1'-chlorovinyl)-1-cyclohexyl-carboxylate was then distilled; this product was in the form of a colourless liquid.

b.p.$_{1\ mm\ Hg}$: 71°–72° C.
Yield: 58%.

(3) 1-(1'-Chlorovinyl)-1-cyclohexyl-carboxylic acid 13 g of methyl 1-(1'-chlorovinyl)-cyclohexylcarboxylate were refluxed with 4 g of potassium hydroxide, 20 cm$^3$ of isopropanol and 10 cm$^3$ of water for 6 hours. A solid was obtained by evaporating off the alcohol and this solid was dissolved in water. The basic aqueous solution was washed with ether and then acidified with dilute hydrochloric acid. The expected 1-(1'-chlorovinyl)-1-cyclohexyl-carboxylic acid was extracted with ether. After evaporating off the solvent, the product was purified by recrystallisation from pentane and colourless crystals were obtained.

m.p.: 60° C.
Yield: 57%.

EXAMPLE 13

1-Bromomethyl-1-cyclohexyl-carboxylic acid

(1) 1-Bromomethyl-1-acetoxymethyl-cyclohexane 55 cm³ of acetic anhydride were added slowly to 65 cm³ of a 48% solution of hydrobromic acid in water. Hydrogen bromide gas was bubbled through the mixture and 74 g of 1,1-dihydroxymethyl-cyclohexane were introduced. The temperature of the solution was raised to 70° C. in the course of 1 hour. The bubbling of hydrogen bromide was ceased. Heating under reflux was continued for 15 hours. The upper phase was separated off, in the cold, and redistilled under reduced pressure. 50 g of 1-bromomethyl-1-acetoxymethyl-cyclohexane were obtained.

b.p.$_{2\ mm\ Hg}$: 112° C.
Yield: 40%.

(2) 1-Bromomethyl-1-hydroxymethyl-cyclohexane 42 g of the 1-acetoxymethyl-1-bromomethylcyclohexane resulting from the preceding stage and dissolved in 80 cm³ of ethanol were heated under reflux for 6 hours, in the presence of 3 cm³ of 48% hydrobromic acid. The ethanol was evaporated off and the oil obtained was distilled. 1-Bromomethyl-1-hydroxymethyl-cyclohexane was obtained.

b.p.$_{2\ mm\ Hg}$: 110° C.
Yield: 70%.

(3) 1-Bromomethyl-1-cyclohexyl-carboxylic acid

A mixture of 16 cm³ of nitric acid (density: 1.38) and 48 cm³ of nitric acid (density: 1.43) was prepared. 0.13 g of ammonium metavanadate, a few crystals of sodium nitrite and then, slowly, 22 g of 1-bromomethyl-1-hydroxymethyl-cyclohexane were added. During the addition, a stream of oxygen was passed into the mixture. The reaction was continued by refluxing the reaction mixture until the nitrous vapours disappeared. The solution was diluted with 50 cm³ of ice-water, whereby 1-bromomethyl-1-cyclohexyl-carboxylic acid crystallised. The acid was purified by recrystallisation from pentane.

m.p.: 71° C.
Yield: 86%.

EXAMPLE 14

Sodium 1-methyl-1-cyclohexyl-carboxylate 0.1 mole of 1-methyl-1-cyclohexyl-carboxylic acid prepared by a method similar to that used in example 7, dissolved in methanol was added to a solution of sodium methylate in dry methanol, prepared using 0.095 mole of sodium and 40 cm³ of methanol as the starting materials. The mixture was heated at 50° C. for 10 minutes and the methanol was then evaporated off in vacuo. The colourless crystals of sodium 1-methyl-1-cyclohexyl-carboxylate were washed with ether, filtered off and dried.

m.p.: >300° C.
Yield: 90%.

EXAMPLES 15 TO 20

A number of sodium salts of the formula

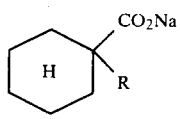

which were prepared by a process analogous to that of Example 14 are listed in Table I below.

TABLE I

| EXAMPLES | R | m.p. in °C.* |
|---|---|---|
| 15 | —C$_2$H$_5$ | >270 |
| 16 | —CH(CH$_3$)$_2$ | >270 |
| 17 | —C≡CH | >270 |
| 18 | —C=CH$_2$<br>\|<br>Cl | >250 |
| 19 | —CH$_2$—C=CH$_2$<br>\|<br>Cl | >250 |
| 20 | —CH$_2$—CH(CH$_3$)$_2$ | |

See Example 21 at the following page.
*The value indicated corresponds to the start of melting, which is frequently accompanied by simultaneous decomposition.

EXAMPLE 22

Sodium 1-allyl-1-cyclohexyl-carboxylate 170 g of 1-allyl-1-cyclohexyl-carboxylic acid (Example 1) were added gradually to a stirred solution, at ambient temperature, of 40 g of sodium hydroxide in 500 g of water in such a way that, at the end of the neutralisation, an aqueous solution of sodium 1-allyl-1-cyclohexyl-carboxylate having a pH of 8 was obtained. 4 g of CECA 2 S charcoal were then added and the mixture was stirred for ½ hour.

The mixture was filtered and the solution was then atomised in order to obtain 184.3 g of sodium 1-allyl-1-cyclohexyl-carboxylate.

m.p.: >250° C.
Yield: 97%.

EXAMPLE 21

Sodium 1-benzyl-1-cyclohexyl-carboxylate 129 g of methanol and then, whilst stirring, 24.6 g of sodium hydroxide pellets were charged into a reactor. The mixture was then stirred until all of the sodium hydroxide had dissolved and the solution was filtered.

Furthermore, a solution of 135 g of 1-benzyl-1-cyclohexyl-carboxylic acid in 300 g of toluene was prepared. The filtered methanolic solution of sodium hydroxide, prepared above, and 4 g of WSL charcoal were then added slowly to this solution, whilst stirring. Stirring was continued for ½ hour after the addition was completed and the mixture was then filtered.

The methanol and the water formed were then removed by distillation and the reaction mixture was cooled to ambient temperature and kept at this temperature for 2 hours, whilst stirring, after which the product was filtered off and dried in a vacuum oven at 50°–60° C. to constant weight.

Weight of sodium salt obtained: 145.8 g.
Yield: 98%.
m.p.: >250° C.

EXAMPLE 23

(a) Preparation of a calcium salt 500 g of purified water and 28 g (0.5 mole) of calcium hydroxide were introduced in a reactor. The mixture was heated up to 70° C. whilst stirring and at that temperature 170 g (1 mole) of 1-isopropyl-1-cyclohexyl carboxylic acid were added all at a time. The mixture was maintained at 70° C. for 2 hours.

The precipitation of the calcium salt was observed. The reaction was then dried in a rotative evaporator in vacuum (water pump). The product was dried in vacuum oven at 65° C. until its weight was constant. The calcium salt was obtained with a yield of 87%.

(b) Preparation of a magnesium salt

The following components were stirred during 4 hours at the ambiant temperature: 1-(1'-chloro vinyl) 1-cyclohexyl carboxylic acid 192.3 g (1.02 mole), magnesia 29.15 g (0.5 mole), purified water 500 g.

The precipitation of the magnesium salt was thus accomplished in the form of a paste. The reaction mixture was dried in a rotative evaporator under reduced pressure of 20 mm Hg (temperature of the water bath: 55°±5° C.). Drying was completed by adding acetone and distillating off this solvent.

Yield: 78%.

EXAMPLE 24

1-(2'-chloro-2'-propenyl)-1-cyclohexyl-carboxamide (1) 1-(2'-Chloro-2'-propenyl)-1-cyclohexylcarbonyl chloride 6 g of thionyl chloride, 10 cm$^3$ of dry benzene and 0.1 cm$^3$ of dimethylformamide were placed in a three-necked flask. 8 g (0.04 mole) of 1-(2'-chloro-2'-propenyl)-1-cyclohexyl-carboxylic acid, dissolved in benzene, were introduced, whilst stirring. The reaction mixture was kept at a temperature of about 30° C. during the addition of the acid and the whole was then refluxed for 8 hours. After evaporating off the benzene, the resulting acid chloride was distilled.

b.p.$_{0.5\ mm\ Hg}$: 86°–87° C.

Yield: 90%.

(2) 1-(2'-Chloro-2'-propenyl)-1-cyclohexylcarboxamide 50 cm$^3$ of liquid ammonia were added to 7 g of the acid chloride prepared in the preceding stage and dissolved in 20 cm$^3$ of ether. The ammonia, and then the ether, were evaporated off and the product obtained was stirred with 50 cm$^3$ of water. The insoluble amide was filtered off, dried and then recrystallised from hexane. It was in the form of colourless crystals.

m.p.: 99°–100° C.

Yield: 70%.

EXAMPLE 25

1-Ethyl-1-cyclohexyl-carboxamide 13.7 g (0.1 mole) of 1-ethyl-1-cyclohexylcarbonitrile and 100 cm$^3$ of 80% sulphuric acid were heated at 100°–105° C. for 5 hours, whilst stirring. The mixture was allowed to cool and was then poured into 400 cm$^3$ of ice-water. The organic phase was extracted with benzene, dried over magnesium sulphate and then concentrated in vacuo. 1-Ethyl-1-cyclohexyl-carboxamide was recrystallised twice from hexane and was in the form of colourless crystals.

m.p.: 73°–74° C.

Yield: 74%.

EXAMPLES 26 TO 32

A number of amides of the formula:

$$\text{cyclohexyl}\begin{array}{c} H \\ R \end{array} CONH_2$$

were prepared by a method analogous to that of Example 24 or 25, as indicated in Table II, below, which also gives their physical constants.

TABLE II

| EX-AMPLE | R | Prepared according to Example | Physical constant |
|---|---|---|---|
| 26 | —CH$_2$Br | 24 | m.p.: 108–109° C. |
| 27 | —CH$_2$—CH=CH$_2$ | 24 | |
| 28 | —CH$_3$ | 25 | m.p.: 65° C. |
| 29 | —CH(CH$_3$)$_2$ | 25 | m.p.: 88.5° C. |
| 30 | —CH$_2$—C≡CH | 24 | m.p.: 35° C. |
| 31 | —CH$_2$—O—CH$_3$ | 24 | n$_D^{20}$ 1.492 |
| 32 | —CH$_2$—(phenyl) | 24 | |

EXAMPLE 33

Sodium 1-isopropoxymethyl-1-cyclohexylcarboxylate

Starting from the 1-isopropyloxymethyl 1-cyclohexyl carboxylic acid prepared in example 5, the same procedure as in example 14 was used to prepare sodium 1-isopropyloxymethyl 1-cyclohexyl carboxylate.

This compound was obtained in the form of a white powder which showed sublimation at 260° C.

EXAMPLE 34

1-isopropyloxymethyl-1-cyclohexyl-carboxamide 10 g of 1-isopropyloxymethyl 1-cyclohexyl carboxylic acid dissolved in 50 cm$^3$ of benzene were heated under reflux for 5 hours together with 15 cm$^3$ of thionyle chloride in the presence of 0.3 cm$^3$ of dimethylformamide.

The acid chloride obtained was purified by distillation (b.p.$_{0.02\ mm\ Hg}$=70° C.), then treated by reaction with liquid ammonia in ether. The amide was distilled (b.p.$_{0.05\ mm\ Hg}$=130° C.), then recrystallized in pentane. A colourless product was obtained.

m.p.=59°–60° C.

yield: 40%.

EXAMPLE 35

1-(3-bromo-2-propynyl)-1-cyclohexyl-carboxylic acid $$\text{cyclohexyl}\begin{array}{c} H \\ CH_2-C\equiv CH \end{array} CO_2H \quad +$$

-continued

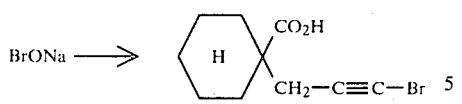

A sodium hypobromite solution was prepared from 5 g sodium hydroxide, 38 cm³ ice water and 2.75 cm³ bromine. The hypobromite solution was added in the cool into 50 cm³ of an aqueous solution of the sodium salt of acetylenic acid (8.3 g = 0.05 mole). The stirring of the mixture was continued between 0° C. and 5° C. for 1 h 30 mn. After washing with hexane, the solution was acidified with diluted HCl until a pH of 4 was reached. The precipitate obtained was washed with water, then dried and recrystallized from heptane. Colourless crystals were obtained.

m.p.: 98° C.
Yield: 35%.

EXAMPLES 36–37

1-vinyl-1-cyclohexyl-carboxylic acid and its sodium salt

The methyl or ethyl 1-hydroxyethyl-1-cyclohexyl carboxylate was dehydrated in the presence of $P_2O_5$ and the ethylenic ester was then hydrolyzed:

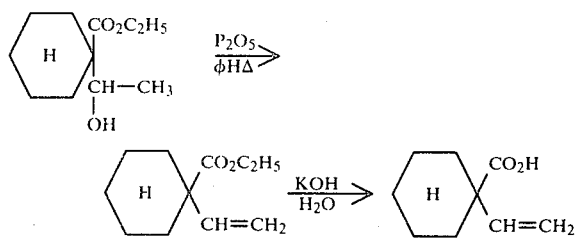

1. ethyl 1-1-hydroxyethyl-1-cyclohexyl-carboxylate

A solution of lithium isopropylamidide was prepared from 300 cm³ butyl lithium 1.5 M in hexane and 52 g of diisopropylamine. At −40° C. 62.4 g (0.4 mole) of ethyl cyclohexyl-carboxylate were added, then at −80° C. 17.6 g of acetaldehyde were also added. The solvent was evaporated off and the mixture was poured into acid ice water. After extraction with benzene the ether was distilled off and a colourless liquid was obtained.

b.p.$_{15\ mm\ Hg}$ = 128° C.-130° C.
Yield: 30%.

The methyl 1-(1-hydroxyethyl)-cyclohexyl-carboxylate can also be obtained by the same procedure.

b.p.$_{13\ mm\ Hg}$ = 120° C.-124° C.

2. Ethyl 1-vinyl-cyclohexyl-carboxylate 12 g (0.06 mole) of ethyl 1-(1-hyroxyethyl)-1-cyclohexyl-carboxylate were heated at 90° C. for 3 hours in 100 cm³ of benzene in the presence of 12 g of $P_2O_5$. The brown benzenic solution was washed in the cool with water, then distilled. The ethyl 1-vinyl-cyclohexyl-carboxylate was obtained with a yield of 55% (6 g) in the form of a colourless liquid.

b.p.$_{14\ mm\ Hg}$ = 90° C.-94° C.

3. 1-vinyl-1-cyclohexyl-carboxylic acid (Example 36)

6 g (0.03 mole) of vinylic ester were heated at 170° C. for 16 hours together with 4.2 g KOH in 20 cm³ of water and 40 cm³ of ethylene glycol. The reaction mixture was then poured into ice water, the aqueous part was washed with hexane, then treated with diluted hydrochloric acid. The acid was distilled and a colourless liquid was obtained.

b.p.$_{12\ mm\ HG}$ = 134° C.-135° C.
Yield: 55%.

4. Sodium 1-vinyl-1-cyclohexyl-carboxylate (Example 37)

This sodium salt was prepared from the acid and obtained in the form of a white powder. m.p. >250° C.

EXAMPLES 38–39

1-(1-chloro-1-methylethyl)-1-cyclohexyl-carboxylic acid and its amide

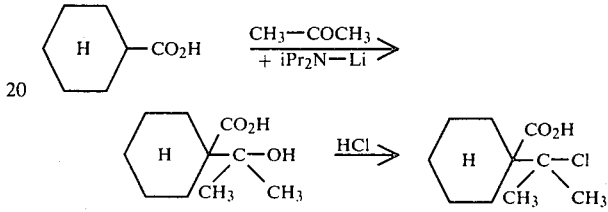

1. 1-(1-hydroxy-1-methylethyl)-1-cyclohexyl-carboxylic acid

A solution of lithium isopropylamide was prepared from 250 cm³ of BuLi 1.6 M in hexane and 40 g of diisopropylamine and 500 cm³ of dried tetrahydrofuranne. 25.6 g (0.2 mole) of cyclohexyl-carboxylic acid were added at −40° C.

The solution was heated at 50° C. for 2 hours, and 12 g dried acetone were then added at −40° C. The reaction mixture was left for 12 hours at the room temperature, and then poured on ice. The aqueous part was washed with ether then treated with HCl 3 N. The acid was extracted with ether then recrystallized from the mixture cyclohexane-benzene (80/20). Colourless crystals were obtained.

m.p. = 115° C.
Yield: 75%.

2. 1-(1-chloro-1-methylethyl)-1-cyclohexyl-carboxylic acid (Example 38)

18.6 g of the acid alcohol prepared were suspended in 100 cm³ of concentrated hydrochloric acid d = 1.19. The mixture was stirred vigorously for 12 hours at the room temperature.

The floating colourless product was filtered, washed several times with water and recrystallized from acetonitrile. Colourless crystals were obtained.

m.p. = 140° C.
Yield: 55%.

3. 1-(1-chloro-1-methylethyl)-1-cyclohexyl-carboxamide (Example 39)

11 g of the chlorinated acid were heated under reflux for 5 hours in 150 cm³ of $CH_2Cl_2$, 5 cm³ of $SOCl_2$ and 0.2 cm³ of dimethylformamide.

The acid chloride obtained was distilled (b.p.$_{0.2\ mm\ Hg}$ = 82° C., Yield: 70%). It was then converted into the amide by heating to 80° C. for 2 h 30 mn in dioxan saturated with ammonia. By evaporating the dioxan off, colourless crystals were obtained which were recrystallized from ethyl acetate.
m.p. = 127° C.-128° C.
Yield: 45%.

EXAMPLES 40-41-42

1-tert-butyl-1-cyclohexyl-carboxylic acid and its salt and amide

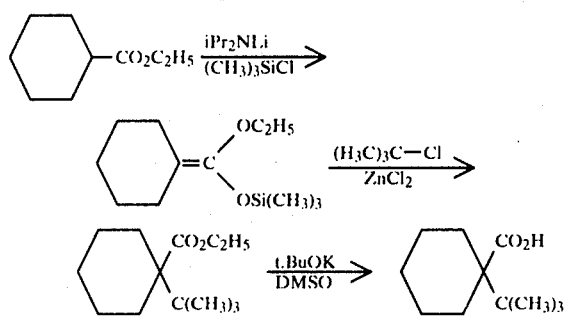

1. Ethyl trimethylsilyl cyclohexyl-centene-acetal

A solution of lithium isopropylamidide was prepared from 312 cm³ BuLi 1.6 M in hexane, 50 g of diisopropylamine and 500 cm³ of tetrahydrofuranne. 78 g (0.5 mole) of ethyl cyclohexyl-carboxylate were added thereto at −10° C., then 62 g of trimethyl silyl chloride.

The precipitate was filtered and the solution was concentrated in vacuum. The acetal was redistilled and a colourless liquid was obtained.

b.p.$_{0.5\ mm\ Hg}$: 76° C.-78° C.
Yield: 90%.

2. Ethyl 1-tert-butyl-1-cyclohexyl-carboxylate 45.6 g (0.2 mole) of the cetene-acetal prepared above, 200 cm³ of dry CH$_2$Cl$_2$, 1.5 g of ZnCl$_2$ and 28 g (0.3 mole) of tert-butyl chloride were kept for 30 hours at the room temperature. The mixture was then poured into 600 cm³ of a cool solution of 5% sodium bicarbonate. The organic part was separated out. The aqueous solutions were washed twice with 100 cm³ methylene chloride. The organic phases were mixed together, then dried and distillated. 18 g of the expected ethyl 1-tert-butyl-1-cyclohexyl-carboxylate were obtained in the form of a colourless liquid.

b.p.$_{0.2\ mm\ Hg}$ = 80° C.-83° C.
Yield: 45%.

3. 1-tert-butyl-1-cyclohexyl-carboxylic acid (Example 40)

33.6 g of t.BuOK in 300 cm³ of anhydrous dimethylsulfoxide and 15.5 g of ethyl 1-tert-butyl-cyclohexyl-carboxylate were heated for 7 hours at 110° C. The mixture was then poured on ice. By acidification with dilute HCl the tert-butyl-cyclohexyl-carboxylic acid was precipitated.

It was recrystallized from acetonitrile and colourless crystals were obtained.
m.p. = 132° C.
Yield: 56%.

4. Sodium 1-tert-butyl-1-cyclohexyl-carboxylate (Example 41)

White powder. m.p. >270° C.

5. 1-tert-butyl-1-cyclohexyl-carboxamide (Example 42)

By reacting SOCl$_2$ with the 1-tert-butyl-1-cyclohexyl-carboxylic acid, the corresponding acid chloride was obtained.

b.p.$_{0.1\ mm\ Hg}$ = 80° C.

After reaction with ammonia, the amide was crystallized from heptane.
m.p. = 137° C.-138° C.

EXAMPLE 43

1-(2,3-dibromo-2-propenyl)-1-cyclohexyl-carboxylic acid

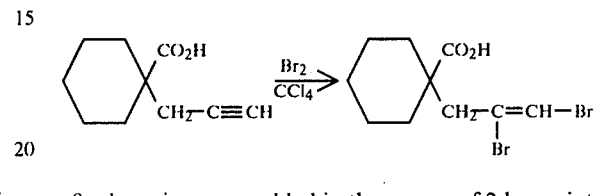

8 g bromine were added in the course of 2 hours into 8.3 g (0.05 mole) acetylenic acid dissolved in 20 cm³ CCl$_4$. Once a colourless solution was obtained, the brominate acid was distilled. A colourless liquid was obtained.

b.p.$_{0.1\ mm\ Hg}$ = 158° C.-160° C.

This product was purified as a solution in CH$_2$Cl$_2$ on a silica gel column, and the sodium salt was then prepared.
Yield: 50%.

EXAMPLE 44

Sodium 1-(2,3-dibromo-2-propenyl)-1-cyclohexyl-carboxylate

This salt was prepared from the acid of Example 43. It was obtained in the form of a white powder. m.p. >250° C.

EXAMPLE 45

1-acetonyl-1-cyclohexyl-carboxylic acid

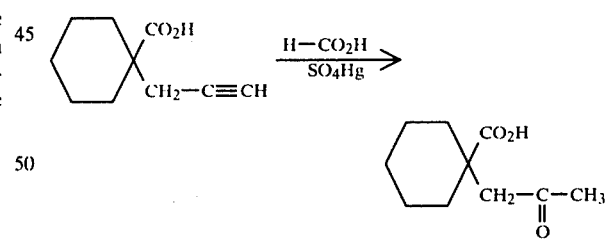

A solution was prepared from 25 cm³ of 85% formic acid and 250 mg mercury sulfate under vigorous stirring at 0° C. In the course of 30 mn 8.3 g (0.05 mole) of acetylenic acid were added. The mixture was left to come back to the room temperature, then a saturated aqueous solution of 40 g ammonium sulfate was added thereto. After extraction with ether and distillation of the cetonic acid, a colourless liquid was obtained.

b.p. $_{0.5\ mm\ Hg}$ = 140° C.-142° C.
Yield: 40%.

The acid was crystallized by cooling down the liquid and it was recrystallized from hexane. Colourless crystals were obtained.
m.p. = 66° C.-67° C.

EXAMPLE 46

Sodium 1-acetonyl-1-cyclohexyl-carboxylate

This salt was prepared from the acid of Example 45. White powder.
m.p. = 224° C.-225° C.

EXAMPLE 47

1-bromoacetonyl-1-cyclohexyl-carboxylic acid

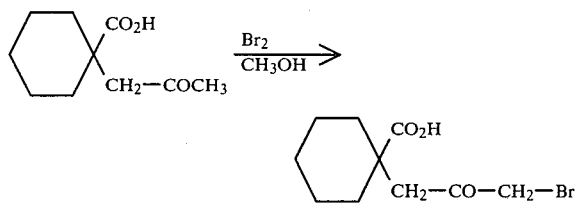

A mixture of 9.2 g (0.05 mole) of cetonic acid, 8 g or bromine and 120 cm³ of methanol is left for 48 hours at the room temperature. The methanol is evaporated off under vacuum and the oil obtained is stirred during 1 hour with 20 cm³ of concentrated hydrobromic acid. The organic part is then separated and washed with water. Pentane is then added in order to crystallize the bromoacetonic acid. The later is recrystallized from cyclohexane in the form of colourless crystals.
m.p. = 83° C.-84° C.
Yield: 40%.

EXAMPLE 48

1-(2-phenoxyethyl)-1-cyclohexyl-carboxylic acid

A solution of lithium diisopropylamide is prepared from 0.4 mole of butyl lithium in hexane, 0.4 mole of diisopropylamine and 300 cm³ of tetrahydrofuran. At −10° C. 0.2 mole of cyclohexyl carboxylic acid is added and the mixture is then heated at 50° C. during 2 hours. At 40° C. 0.2 mole of 1-bromo-2-phenoxyethane is added. The reaction mixture is treated with diluted hydrochloric acid, the acid is extracted with ether. It is purified by recrystallization from cyclohexane and obtained as colourless crystals.
m.p. = 110° C.-111° C.
Yield: 50%.

EXAMPLES 49 TO 55

By salification or amidification of the acids, the following compounds are prepared by the same procedures as already described.

EXAMPLE 49

1-isobutyl-1-cyclohexyl-carboxamide from the acid of example 10.

EXAMPLE 50 sodium 1-propargyl-1-cyclohexyl-carboxylate from the acid of example 3.

EXAMPLE 51

1-vinyl-1-cyclohexyl-carboxamide from the acid of example 36.
b.p. $_{12\ mm\ Hg}$ = 87° C.-88° C.
m.p. = 36° C.-37° C.

EXAMPLE 52

1-ethynyl-1-cyclohexyl-carboxamide from the acid of example 11.
b.p. $_{12\ mm\ Hg}$ = 96° C.-97° C.
m.p. = 78° C.-79° C.

EXAMPLE 53

Sodium 1-(2-phenoxyethyl)-1-cyclohexyl carboxylate from the acid of example 48. White powder. m.p. = 208° C.-209° C.

EXAMPLE 54

1-(2-phenoxyethyl)-1-cyclohexyl-carboxamide from the acid of example 48, through the acid chloride (b.p. $_{0.05\ mm\ Hg}$ = 152° C.). Appearance: white crystals. m.p. = 117° C.-118° C.

EXAMPLE 55

Sodium salt of the acid of example 4.

EXAMPLES 56 TO 61

According to the procedure described in Example 36 for preparing the acid, then by salification or amidification of the acid according to the procedure described above, the following compounds are prepared:
(1) On one hand in succession:
  methyl 1-(1-hydroxy-1-propyl)-cyclohexyl-carboxylate.
  Colourless liquid. b.p. $_{12\ mm\ Hg}$ = 130° C.-132° C. Yield = 80%.
  methyl 1-(1-propenyl)-cyclohexane-carboxylate.
  Colourless liquid. b.p. $_{12\ mm\ Hg}$ = 100° C. Yield = 45%.
  1-(1-propenyl)-cyclohexyl-carboxylic acid (Example 56).
  Purified by distillation. b.p. $_{12\ mm\ Hg}$ = 146° C.-148° C. Yield = 75%.
  The acid crystallises slowly. m.p. = 56° C.-57° C.
  sodium 1-(1-propenyl)cyclohexyl-carboxylate (Example 57).
  m.p. > 250° C.
  1-(1-propenyl)-cyclohexyl-carboxamide (Example 58).
  m.p. = 61° C.-62° C. (after recrystallisation from pentane).
(2) On another hand in succession:
  methyl 1-(1-hydroxy-1-methylethyl)cyclohexyl-carboxylate.
  Colourless liquid. b.p. $_{12\ mm\ Hg}$ = 124° C.-126° C. Yield = 70%.
  methyl 1-isopropyl-cyclohexyl-carboxylate.
  Colourless liquid. b.p. $_{12\ mm\ Hg}$ = 98° C.-100° C. Yield = 80%.
  1-isopropenyl-cyclohexyl-carboxylic acid (Example 59).
  b.p. $_{12\ mm\ Hg}$ = 146° C.-147° C. Yield = 50%.
  sodium 1-isopropenyl-cyclohexyl-carboxylic acid (Example 60).
  m.p. > 250° C.
  1-isopropenyl-cyclohexyl-carboxaide (Example 61).
  m.p. < 50° C. b.p. $_{0.5\ mm\ HG}$ = 106° C.-108° C.

PHARMACOLOGICAL TESTS

The compounds of the invention have central nervous system activity and, in particular, valuable anticonvulsant and/or antianoxia and/or antipsychotic properties. The pharmacological study was carried out on a representative sample of compounds of formula (1), that is to say on the compounds listed in the following Tables in which the signification of the variables of the formula, the number of the Example describing the preparation of the compounds are indicated.

The compounds were administered as follows:
the acids: in solution in Labrafil, a trade name denoting a mixture of polyoxyethylated oleic acid glycerides;
the sodium salts: in aqueous solution; and
the sodium salts: in aqueous solution; and
the amides: as a 30% solution in propylene glycol.

The various tests to which the studied compounds were submitted are hereinafter described.

Pentetrazole seizure

This test was carried out on batches of 10 male OF1 mice which had fasted since the day before and were placed in individual cages, in accordance with the method of Cheymol (J.) *Acta. Pharmacol.*, (1950), 2, 1–55.

The treatments were carried out perorally 15 minutes before intraperitoneal (i.p.) injection of a solution of pentetrazole (125 mg/kg).

The mortality is recorded 3 hours after this injection.

Maximum electrical seizure

The technique used is that recommended by GOODMAN (L. S.), SING-GREWALD (M.), BROWN (V. C.) and SWINYARD (E. A.), *Am. J. of Pharmacol. and Ther.*, (1953), 168–175, namely using intraauricular electrodes coated with conducting paste and stimulation by a voltage varying from 10 to 50 volts in rectangular waves of 0.2 second.

The animals tested are male Swiss mice grouped into batches of 10. The normal threshold of the electric shock which is capable of causing tonic extension of the front paws is first determined for each animal. It is at about 20–25 volts for mice.

The animals are selected the day before the test and, the next day, after trebling the threshold voltage, the percentage to which the tonic seizures are inhibited in the case of the animals which have previously been treated with the product to be tested is noted.

Ouabain seizure

Ouabain was administered intra-ventricularly at a dose of 5 γ/mouse in a volume of 0.02 ml. The general seizure occurs on average 2 to 3 minutes after the injection.

β-Mercaptopropionic acid seizure

β-Mercaptopropionic acid is an inhibitor of glutamatedecarboxylase (GAD), which is an enzyme which catalyses the conversion of glutamate to γ-aminobutyric acid (GABA). Its action thus manifests itself in a lowering of the GABA level and the occurrence of general tonico-clonic seizures 3 to 4 minutes after it has been administered. β-Mercaptopropionic acid was administered to mice intraperitoneally at a dose of 40 mg/kg.

Anoxia as a result of confinement

Mice (in batches of 20) are placed in a 200 cm$^3$ hermetically sealed chamber (a wide-mouthed glass vessel) which is under normal pressure and has a normal content of atmospheric oxygen. All of the treatments are administered intraperitoneally immediately before introduction into the chamber. The animal is considered to be dead at the moment when breathing stops.

Since the wide-mouthed vessels chosen are very small, the motor activity of the animals is extremely low and this eliminates, in principle, the possibility of a positive result due to a sedative effect.

Therefore, the percentage increase in the survival time of the treated animals is noted, relative to the batch.

Sedative activity: Rotarod test, BOISSIER (J. R.) Therapie (1958), 13, 1,074.

This test is used for the purpose of assessing the ability of the animals to coordinate their movements. It uses a wooden cylinder which has a diameter of 4.8 cm and revolves at a speed of 4 revolutions/minute. The test is carried out on male mice weighing about 22 g. The products are administered perorally (p.o.) to batches of 10 animals per dose. The animals are placed on the apparatus 15 minutes after administration of the product. The percentage of mice which lose their equilibrium reflex, that is to say which become incapable of retaining their balance on the cylinder for a period of 2 minutes, is noted.

Using the regression straight line method, a 50% neurotoxic dose (NTD 50) is calculated, which thus expresses the average level of the first neuromuscular effects under the influence of the studied product.

Acute toxicity

In order to locate the boundary separating the pharmacological effects from the toxicity of the products, a very approximate assessment of the toxicity was carried out on mice (batches of 10 animals) after peroral treatment.

The results of the tests are listed in the table which follows. It is to be noted that the 50% effective doses (ED$_{50}$), where these have been determined, were calculated by the method of MOOD (*J. Am. Statist. Assoc.*, (1965), 60, 967–78).

TABLE III

Compared anticonvulsivant properties.
Pentetrazole crisis test, 15 minutes after administration.

|  | DE 50 mg/kg |
|---|---|
| Reference compound: | |
| Depakene ® (Reg. Trade Mark of Labaz, Paris) (sodium dipropyl-acetate). | 142 |
| Compounds according to the invention: | |
| Example 15 | 120 |
| Example 16 | 110 |
| Example 41 | 131 |
| Example 37 | 95 |
| Example 50 | 120 |

TABLE IV (1)

| Tests carried out | Products studied: Example n° | | | | | |
|---|---|---|---|---|---|---|
|  | 22 | 18 | 17 | 50 | 19 | 55 |
| Anticonvulsant activity measured 15 minutes after peroral treatment | | | | | | |
| 1. Pentetrazole seisure, ED$_{50}$ | | 40% at | 30% at | | | |

TABLE IV (1)-continued

| Tests carried out | 22 | 18 | 17 | 50 | 19 | 55 |
|---|---|---|---|---|---|---|
| in mg/kg or % protection | 154 | 200 mg/kg | 170 mg/kg | 120 | 94 | 190 |
| 2. Maximum electrical seizure ED$_{50}$ in mg/kg or % protection | 80% at 200 mg/kg | — | 13% at 170 mg/kg | 478 | 366 | 0% at 190 mg/kg |
| 3. Ouabain seizure, ED$_{50}$ in mg/kg or % protection | 638 | 851 | 933 | 507 | 579 | 950 |
| 4. β-Mercaptopropionic acid seizure, ED$_{50}$ in mg/kg or % protection | — | — | — | 245 | 300 | — |
| Anti-anoxia activity, intraperitoneal treatment | | | | | | |
| 5. Anoxia as a result of confinement, % increase in the survival time | 59% at 240 mg/kg | 40% at 260 mg/kg | 23% at 210 mg/kg | 48% at 280 mg/kg | 45% at 240 mg/kg | 22% at |
| 6. Sedative activity, peroral treatment, Rotarod test, ED$_{50}$ in mg/kg or % of failures | 20% at 600 mg/kg | 0% at 600 mg/kg | 0% at 500 mg/kg | 40% at 550 mg/kg | 30% at 700 mg/kg | 0% at 600 mg/kg |
| 7. Acute toxicity % mortality | — | — | — | 10% at 950 | 10% at mg/kg | 1100 mg/kg |

TABLE IV (2)

| Test No. | 21 | 27 | 29 | 30 | 24 | 31 | 32 |
|---|---|---|---|---|---|---|---|
| 1 | 116 | 20 | 15 | 65 | 57 | 195 | 32 |
| 2 | 431 | 55 | 70 | 91 | 101 | 200 | 115 |
| 3 | 638 | 66 | 31 | 170 | 96 | 250 | 200 |
| 4 | 257 | 38 | 12 | — | 64 | — | 200 |
| 5 | 44% at 170 mg/kg | 0% at 50 mg/kg | 16% at 25 mg/kg | — | 0% at 50 mg/kg | — | 0% at 50 mg/kg |
| 6 | 650 | 75 | 35 | 125 | 125 | 300 | 125 |
| 7 | 20% at 1,000 mg/kg | 100% at 500 mg/kg | 100% at 500 mg/kg | 20% at 500 mg/kg | 20% at 500 mg/kg | 0% at 500 mg/kg | — |

TABLE IV (3)

| Test n° | 14 | 28 | 42 | 37 | 26 | 39 | 44 | 35 | 46 | 47 | 54 |
|---|---|---|---|---|---|---|---|---|---|---|---|
| 1 | 317 | 178 | 79 | 95 | 75 | 66 | 240 | 335 | 300 | 0 at 395 mg/kg | 198 |
| 2 | 563 | 311 | — | — | — | — | 60% at 600 mg/kg | 20% at 735 mg/kg | | | |
| 3 | 600 | — | — | — | — | — | >900 | — | >900 | | |
| 4 | 118 | 100 | 95 | | 46 | 63 | 340 | 30% at 400 mg/kg | 270 | 30% at 400 mg/kg | 86 |
| 5 | 29% at 160 mg/kg | 30% at 70 mg/kg | | | 6 at 50 mg/kg | | 50% at 190 mg/kg | | | 24% at 130 mg/kg | 25% at 100 |
| 6 | 1017 | 425 | — | | 125 | | 280 | 245 | 0% at 600 mg/kg | 0% at 790 mg/kg | 160 |
| 7 | 50% at 1882 mg/kg | 50% at 752 mg/kg | | | 0% at 500 mg/kg | | 0% at 600 mg/kg | 0% at 735 mg/kg | | 30% at 790 mg/kg | |

It is evident from the results obtained that the compounds studied can be used in therapy as antiepileptic agents, antianoxic agents and antipsychotic agents and in the treatment of various psychic and neurological conditions in children, adults or elderly people, such as, for example, disturbances of alertness, memory, attention, affectivity, character and speech, motor and cerebral deficiencies and the like.

It must nevertheless be understood that the present invention is not limited to the particular compounds described in details in their physico-chemical and/or pharmacological properties, nor to particular modes of preparation of such compounds.

What is claimed is:

1. A method of inducing anticonvulsant, antianoxic or antipsychotic effects in a human needing such treatment, comprising administering to said subject a dosage ranging from 200 to 3000 milligrams per day of a cyclohexane derivative of the general formula:

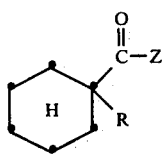

wherein Z is a hydroxyl group or an —OM group wherein M represents an alkali metal atom or an equivalent of an alkaline earth metal, and R is a linear- or branched-chain alkyl radical having from 1 to 9 carbon atoms and optionally substituted by one or more halogen atoms.

2. A method according to claim 1 wherein the anticonvulsant action is antiepileptic.

3. A method according to claim 1 wherein R is methyl, ethyl, propyl or butyl.

* * * * *